United States Patent [19]

Jones

[11] 4,286,754

[45] Sep. 1, 1981

[54] CONTROLLED-RATE LIQUID DISPENSER

[75] Inventor: Cheryl D. Jones, Woodbury, Minn.

[73] Assignee: Minnesota Mining and Manufacturing Company, St. Paul, Minn.

[21] Appl. No.: 685,116

[22] Filed: May 10, 1976

[51] Int. Cl.$^3$ ............................................... A61L 9/00
[52] U.S. Cl. ...................................... 239/6; 239/44
[58] Field of Search ........................... 239/34, 41–47, 239/49–51.5, 54, 55, 57–59, 145, 6; 181/33 GA

[56] References Cited

U.S. PATENT DOCUMENTS

| 1,129,897 | 3/1915 | Owen | 239/45 |
|---|---|---|---|
| 1,763,678 | 6/1930 | Smith | 239/54 X |
| 2,596,659 | 5/1952 | D'Eustachio | 181/33 GA |
| 2,631,890 | 3/1953 | Fink | 239/47 |
| 2,691,615 | 10/1954 | Turner et al. | |
| 2,806,509 | 9/1957 | Bozzacco et al. | 181/33 GA |
| 2,978,340 | 4/1961 | Veatch et al. | 181/33 GA |
| 3,166,615 | 1/1965 | Farrell | 264/279 X |
| 3,175,935 | 3/1965 | Vanstrum | 156/24 X |
| 3,550,853 | 12/1970 | Gray | 239/44 |
| 3,587,968 | 6/1971 | Hennart et al. | 239/47 |
| 3,652,197 | 3/1972 | Tokarz | 431/326 |
| 3,753,500 | 8/1973 | Voegeli | 210/446 |
| 3,770,199 | 11/1973 | Hoek et al. | 239/54 |
| 3,978,176 | 8/1976 | Voegeli | 261/122 |

FOREIGN PATENT DOCUMENTS

| Ad.26727 | 11/1923 | France | 239/44 |
|---|---|---|---|
| Ad.29206 | 3/1925 | France | 239/44 |

Primary Examiner—Andres Kashnikow
Attorney, Agent, or Firm—Cruzan Alexander; Donald M. Sell; Roger R. Tamte

[57] ABSTRACT

Liquid is dispensed at a uniform rate over an extended period of time through use of a distinctive wicking structure that comprises a matrix of closely packed, solid particles bonded together with a bonding material that only partially fills interstices between the particles and thereby leaves a uniform interconnected network of pores.

14 Claims, 4 Drawing Figures

CONTROLLED-RATE LIQUID DISPENSER

BACKGROUND OF THE INVENTION

Most prior-art methods for dispensing volatile air-freshening liquids—e.g. by pulling a portion of a long, fibrous wick from a container that is filled with a highly diluted liquid, or spraying the liquid from an aerosol can—are limited to uses in which the liquids are applied for rather brief, incremental periods. The rapid evaporation of the liquids used in these methods, and the unequal rates of evaporation of their constituents, prevent the methods from maintaining adequately uniform air freshening over long periods of time.

Many persons have recognized and sought to satisfy a need for longer-term air-freshening. Solid air-treating gels comprising a fragrant volatilizable substance, large amounts of water, and a gelling agent (see Turner et al, U.S. Pat. No. 2,691,615, issued in 1954) are one such attempt. But even these gels do not maintain uniform air freshening, as indicated by the suggestion in Turner et al that the gel be segmented so as to provide fresh surfaces for evaporation at later stages in use of the gel.

Others have proposed more elaborate arrangements, but without achieving widespread utility. For example, Hoek et al, U.S. Pat. No. 3,770,199, teaches a dispensing device that comprises a porous tubular member, with pores so fine that the member holds the liquid to be dispensed, and an impermeable tubular member telescoped around the porous member. Besides being rather complicated in structure, this device is limited in the kind of liquids that can be dispensed and the situations in which it can be used, since vaporization must occur within the tubular member and the vapors then transmitted through the walls of the tubular member.

Another example is Gray, U.S. Pat. No. 3,550,853, which seeks to provide controlled release of volatiles by wicking liquid through a resilient polyurethane open-cell foam compressed to a predetermined extent. However, the lack of uniformity in pore size, the comparatively low level of connection between cells, and the variation in the nature of the foam over a period of use limits uniformity in release of vapor.

SUMMARY OF THE INVENTION

The present invention provides a new dispenser that makes novel use of a distinctive porous structure as a wick, this porous structure having structural features that make it effective to dispense liquids at a uniform rate in spite of the long-recognized deficiencies of prior-art wicking materials as liquid dispensers. Briefly, a wicking structure as used in this invention comprises a matrix of closely packed, solid particles adhered together so as to leave an interconnected network of pores. The particles in a particular porous wicking structure are within a narrow range of sizes and are bonded together so as to substantially maintain their original configuration, with the result that the pores are quite uniform in size. This uniformity and control of pore size has been found to result in a uniform, controlled release of liquid stored within the pores.

A preferred method for making a porous wicking structure as described is to coat individual matrix particles with a thin coating of tack bonding material; then cover that tacky bonding material with a solid pulverized nontacky bonding material (to produce a coated particle as described in Vanstrum, U.S. Pat. No. 3,175,935); and then place the coated particles in a mold and compact them under elevated temperature conditions. The bonding material coated on the particles flows to form a thin coating on the individual particles, with the coatings fused together at their points of contact. The bonding material only partially fills the interstices between the particles, whereby the interconnected network of pores is formed.

Porous structures of the general type described are known in the art; for example, they have been previously used as filters (see Voegli, U.S. Pat. No. 3,753,500), and as mold structures (see Farrell, U.S. Pat. No. 3,166,615). Somewhat similar, though also significantly different, structures, i.e., porous polyethylene, porous ceramic, and porous stainless structures are also known (made by compacting particles of polyethylene, etc. with heat and pressure, whereupon the particles fuse together, but generally leaving less uniformity in porosity than obtained with the preferred method described above); and one use that has been proposed for such structures is as foamers in foam-dispensers (when a foamable liquid is forced into the porous structure in combination with an air stream, a foam is dispensed from the porous structure). Still another porous structure (using hollow ceramic spheres as the matrix particle) has been suggested for use as a nonconsumable buoyant flame wick for candles (see Tokarz, U.S. Pat. No. 3,652,197; the wick floats on a flammable liquid such as molten wax, and transmits the flammable liquid by capillary action).

However, none of these prior uses of porous structures involved the unassisted dispensing of vapors or of any material like vapors from a porous structure having a highly uniform porosity. In fact, some of the prior porous structures would not be suitable for dispensing vapors according to the present invention (e.g. because of too fine a porosity); and in some cases dispensing of vapors would be undesired (e.g. vaporization not assisted by a burning flame would apparently cause undesired spreading of the flame on the buoyant wick). The present invention involved a new discovery about porous structures as used in the invention, namely that liquid will volatilize from these structures at a uniform rate over an extended period of time. As the above discussion of background work in vapor-dispensing reveals, this discovery overcomes problems that have existed in the vapor-dispensing art for many years, and as a result makes an important advance in that art.

A dispenser of the invention may be self-contained, i.e. have the liquid to be dispensed totally stored within the porous structure; or the porous structure may be used in combination with a container for storing additional liquid that is to be dispensed. The container is generally closed except for an opening adapted to tightly receive the porous structure. The porous structure is positionable within the opening, with a portion of the porous structure exposed outside the container, and with another portion extending into the liquid stored within the container.

While the invention is particularly useful to dispense volatile liquids in vapor form, dispensers of the invention are also useful to dispense liquids in liquid form, e.g. to dispense medicines or reactant ingredients into a liquid stream. In such a use, the wicking structure extends into a conduit or other container where it is immersed into the liquid into which the liquid from the wicking structure is to be dispensed.

DETAILED DESCRIPTION

Figure 1:
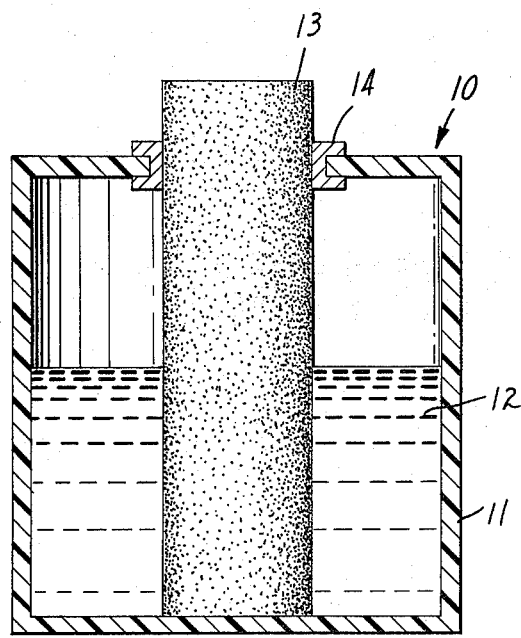
FIG. 1 is a sectional schematic diagram of an illustrative dispenser of the invention.
Figure 2:
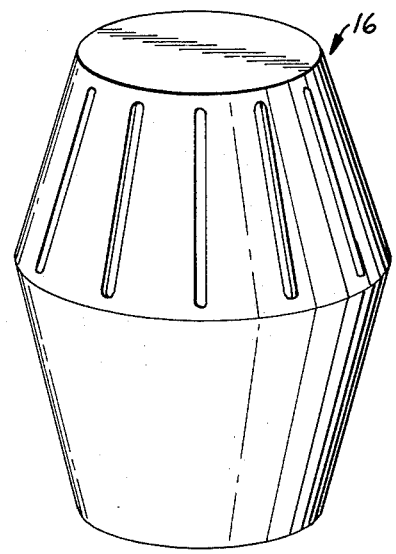
FIG. 2 is a perspective view of a different illustrative dispenser of the invention.

FIGS. 1 and 2 show illustrative dispensers of the invention. The dispenser 10 of FIG. 1 comprises a container 11 which holds a liquid 12 to be dispensed, a wicking structure 13 partly immersed in the liquid 12 but also extending out to the exterior of the container 11, and a gasket 14 that seals the opening between the dispensing element 13 and the container 11.

The dispenser 16 of FIG. 2 is self-contained and comprises a wicking structure in which a volatile liquid material to be dispensed is stored.

Figure 3:
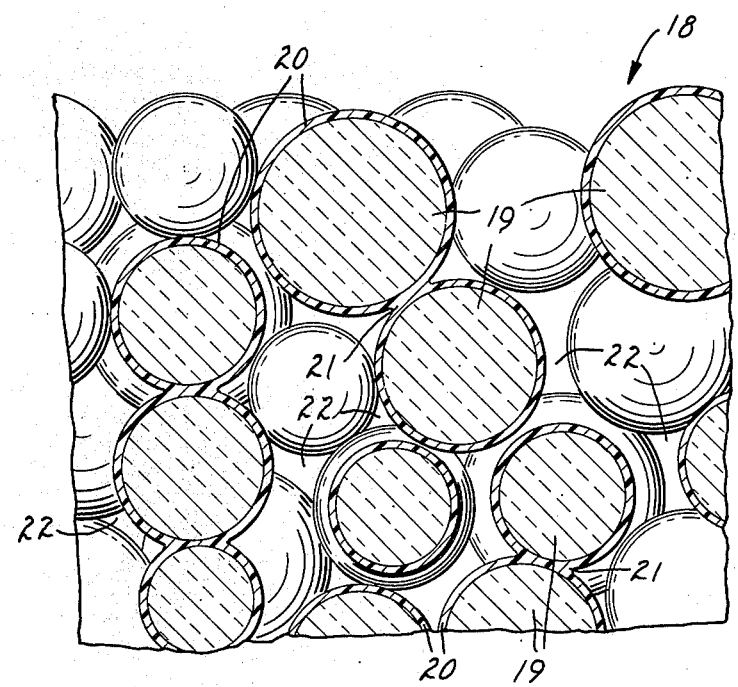
FIG. 3 is an enlarged sectional view through an illustrative porous structure useful as a wicking structure in the present invention.

FIG. 3 shows an enlarged cross section through a representative porous structure 18 used as a wicking structure in the invention. The porous structure 18 comprises a matrix of closely packed microspheres 19, which are each coated with a thin layer 20 of bonding material. The individual layers of bonding material 20 are fused together at their points of contact 21, whereby they bond the microspheres 19 together. The bonding material only partially fills the interstices between the microspheres, leaving an interconnected network of pores 22.

As previously indicated, a preferred method of forming a structure such as shown in FIG. 3 is to coat the matrix particles with a thin coating of tacky bonding material; then cover that tacky bonding material with solid particulate nontacky bonding material; and then compact the particles under elevated temperature conditions, whereupon the bonding material flows to form thin layers, such as the layers 20 of FIG. 3, fused together at their points of contact. The resulting continuous covering of the matrix particles with thin layers of bonding material provides desired uniformity in the surface defining the porous network.

Alternatively, all of the bonding material may be directly coated on the particles as a thin layer, and these particles then consolidated together (see Farrell, U.S. Pat. No. 3,166,615). Or solid particulate bonding material and matrix particles without a tack coat may be mixed together and then consolidated with heat and pressure. Whatever method is used, a product is formed in which the particles form a closely packed matrix (i.e. the particles are typically in near-contact, separated from their nearest neighboring particles by no more than 50 percent of their diameter so as to provide an interstitial structure between the particles) bonded together so as to only partially fill the interstices between the particles.

Rounded particles such as round sand granules, and preferably spherical particles, are the best matrix particle because of the greater uniformity in porosity achieved and because rounded particles can be conveniently handled and closely packed together even when in small sizes. The particles should be solid in contrast to liquid (they may be hollow or porous) and preferably are not deformable at at least moderate compacting pressures such as 200–1000 pounds/square inch (14–70 kg/square cm) to allow the use of such pressures to form a "green" compact. The matrix particles also should not flow during a curing operation, in order to maintain a desired control of porosity.

The best uniformity in porosity is obtained, as previously noted, by using matrix particles that are uniform in size. For that reason, the matrix particles preferably have a diameter that is within plus-or-minus 20 percent of the mean diameter of the particles. However, because the particles are sized by screening methods, the actual spread of diameters may be somewhat greater. The size of the particles may be varied to obtain varied properties, and differently-sized particles may be used in the same dispenser, as in discrete layers.

Generally the matrix particles will be between about 10 and 1000 micrometers in average diameter to achieve desired control over volatilization of a liquid to be dispensed, and preferably they will be between 150 and 600 micrometers in average diameter. The size of the particles is surprisingly important to the results; for example, although two wicking structures may be made in the same manner with the same narrowness in size range of particles to give comparative uniformity in porosities, one of the wicking structures will provide much more uniform dispensing of a particular liquid. Thus, with a conventional fragrance such as Reynaud's Jasmine, a much more uniform rate of dispensing is obtained with particles in the size range 150–600 micrometers, particularly in the 150–300 micrometer range. The multicomponent nature of especially olfactory liquids may contribute to this result, but whatever the explanation, an optimum size can be empirically determined for a particular liquid to be dispensed.

Glass microspheres are preferred as at least the major particle in the matrix (i.e. comprising at least a majority by weight of the matrix particles), since glass has good compressive strength; it has a broad resistance to attack by liquids that may be impregnated into the porous structure; it is readily formed into spherical shapes and desired sizes; and it can be obtained inexpensively. Other useful crush-resistant, or nonfriable matrix particles which may be used in whole or part include inorganic particles such as sand granules; organic polymeric particles, which are preferably in a cured form at least in the completed dispensing structure; and metal particles.

A variety of different bonding materials can be used to bond the matrix particles together. As a general rule, the bonding material is different from the matrix particles at least in flow characteristics during manufacture of the dispensing structure: at some point in the manufacturing process, the bonding material generally flows and fuses or blends with itself. In a completed structure, the bonding material is solid and insoluble and substantially inert in a volatile liquid that is to be dispensed from the porous structure. Organic bonding materials are typically used, and preferably they are thermosetting or curing materials, that is, they chemically react to become relatively infusible and insoluble. Epoxy resins, i.e. organic materials having more than one, 1,2-epoxy group per molecule, are preferred and may take the form inter alia, of polyglycidyl ethers of polyols such as bisphenol A; so-called novolac epoxies; and cycloaliphatic epoxies. Besides epoxy resins, other useful bonding materials include polyesters, polyurethanes, phenolics, and such inorganic materials as silicates.

The use of a bonding material different from the matrix particles means that the matrix particles generally are not deformed during manufacture of the wicking structure, and this lack of deformation contributes to the maintenance of uniform porosity. Thus, even if the bonding material differs from the matrix particle only in flow characteristics (e.g. particles uniform in chemical composition are adhered together, with only a thin layer at the outer surface of the particle, i.e. the bonding material, flowing and fusing with a similarly thin layer on other particles so as to leave an interconnected porosity), a central core or matrix particle generally remains undeformed.

In addition to the previously noted effect of particle size and shape on porosity, porosity can also be controlled by controlling the amount of bonding material in the dispensing structure. To maximize the capacity of the dispensing structure, porosities of 20–50 volume-percent are used, but to provide a strong dispensing structure the porosity preferably does not exceed 35 volume-percent of the structure.

Figure 4:
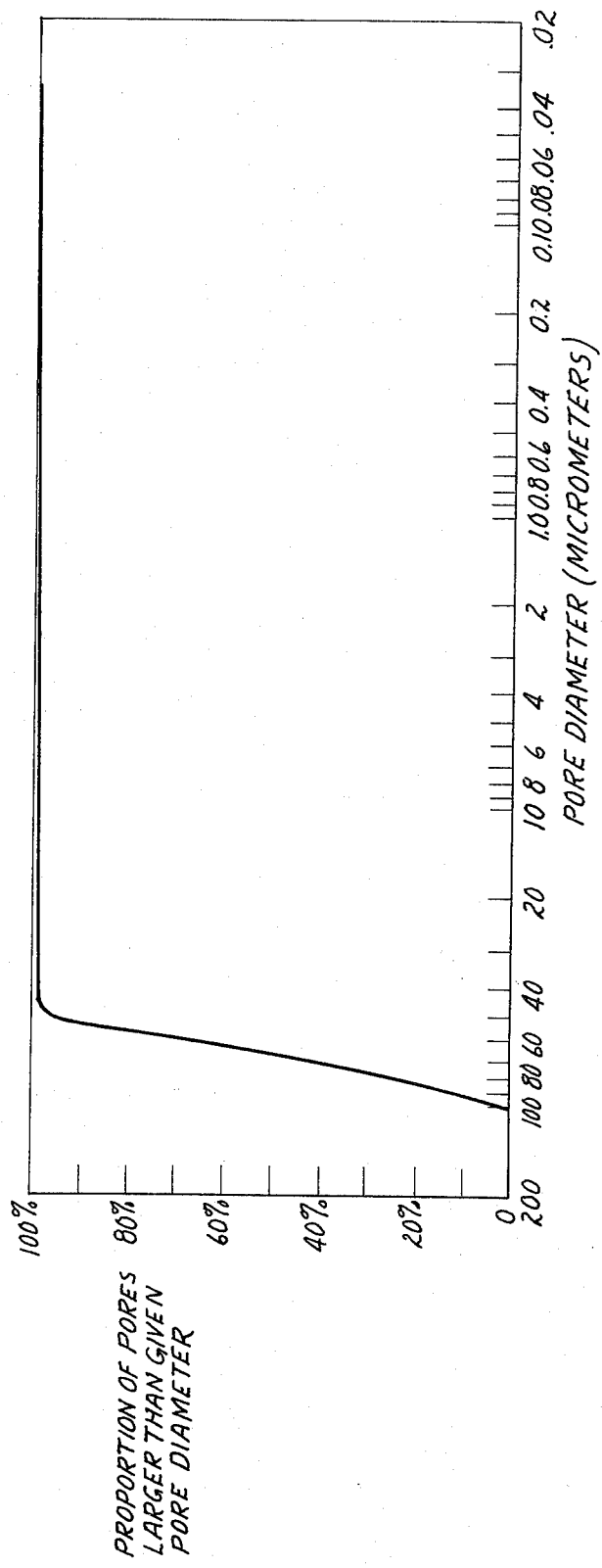
FIG. 4 is a plot obtained from a porosimeter and shows the percentage of pores having certain pore sizes for a representative wicking structure used in the invention.

The uniformity in porosity that generally characterizes wicking structures of the invention is represented in FIG. 4, which is a graph of porosimetry data obtained by measuring Sample A of the subsequently described example with an Aminco-Winslow porosimeter. Pore diameter in micrometers is plotted logarithmically on the abscissa, and percentage of pores having a pore diameter greater than that given on the abscissa is plotted in percent on the ordinate (the percent numbers are converted from volumes of mercury measured on the porosimeter). The sharp slope of the curve means that the bulk of the pores are within a relatively narrow range of pore sizes; in this case, most of the pores have a diameter between 50 and 100 micrometers and the pores average about 65 micrometers in diameter.

Dispensers of the invention are useful with a wide variety of liquids that have a function when emitted as vapor into a fluid, usually air, but alternatively oxygen-rich atmospheres, inert gases, etc., surrounding the dispenser. Such liquids include fragrances, deodorizers, counteractants, masking agents, neutralizers, and other agents having an olfactory function; insecticides; medicaments; disinfectants; and the like. Typically, the liquids have no function within the dispenser, but function in the intended way only after they have been emitted from the dispenser.

Dispensers of the invention are especially adapted for use with liquids having an olfactory function, and they offer the opportunity to dispense vapors from such liquids when the liquids are in a concentrated or minimally diluted form (e.g. with at least 50 weight-percent, and preferably 75 weight-percent being active olfactory agents). Commercial liquids used to provide a fragrance to the air (e.g. perfumes, air-fresheners) are generally prepared by blending basic raw materials which include odoriferous essential oils (volatile oils isolated from an odorous plant), extracts from wood, gums, resins, animal secretions, and synthetics. The basic raw materials are typically very complex mixtures of compounds, which often cannot be fully analyzed into known chemical formulations.

Most often the liquids are to be dispensed in small daily amounts, usually amounting to only a small portion (often on the order of one percent or less) of liquid stored within the porous or wicking structure. However, the amount of the liquid needed to perform its function in the fluid surrounding the dispenser can vary widely. For example, a few parts of a fragrance per million parts of air may be effective to provide a desired fragrance to the air; while a larger amount of vapor may be needed for insecticide or medicinal purposes. While volatility of liquids to be dispensed can vary widely, almost always a volatile substance to be dispensed from a dispenser of the invention will have a volatility sufficient to maintain a concentration of 1 or 2 parts per million parts of air in a still room at a distance of about five feet from the dispenser. Also, most often a dispenser having a porous structure immersed in a liquid, with a surface area of about 50 square centimeters exposed to the air (in a still room), will often dispense on the order of at least 0.1 gram of volatile liquid in a day, and more typically about 0.5 gram.

The liquid to be dispensed also should be capable of being wicked into and through the porous structure. For best results, the liquid should have a viscosity at a temperature of use, typically room temperature, of less than 100, and preferably less than 20 centipoises. To achieve such a viscosity the liquid may be diluted with a volatile diluent; however, as noted above, commercial perfume concentrates can be used in undiluted form, with the result that the rate at which the active fragrant ingredient is dispensed into the air is more uniform and controlled.

The invention will be further illustrated by the following example.

Twenty pounds (9.1 kg) of glass microspheres having diameters from 177 to 250 micrometers (Potters Industries "Ballotini Impact Beads") were given a tacky coating of bonding material by mixing them in 2 pounds (0.9 kg) of a solution consisting of 25.3 parts (by weight) of diglycidyl ether of bisphenol A ("Epon 828," available from Shell Chemical Company), 8.27 parts of a higher-molecular-weight diglycidyl ether of bisphenol A ("Epon 1001"), 6.74 parts of isophthalyldihydrazide, 15.6 parts of titanium dioxide, 1.04 parts of an amino-substituted bentonite, 1.62 parts of toluene, and 41.1 parts of 2-butanone, and 0.32 part of an aminosilane (Dow-Corning Z-6020). The mixing was performed in a "Hobart" mixer, set at low speed, for 10 minutes.

To this mixture was added 10 pounds (4.5 kg) of a powdered B-staged curable organic bonding material. This bonding material included 71.5 parts of a diglycidyl ether of bisphenol A ("Epon 1002") modified with a few-tenths of a part of a modified acrylate, which is a leveling agent commercially available under the trade name "Modaflow" from Monsanto Company; 0.46 part of tri(dimethylaminoethylphenol), which is a curative available under the trade name "DMP-30" from Rohm and Haas; 5.69 parts of a catalyst blend comprising about 4 parts by weight isophthalyldihydrazide, 1 part dicyandiamide, and 22.6 parts of pigment to provide the desired color and opacity. The pulverized bonding material coated glass microspheres were mixed in the "Hobart" mixer about 5 minutes at low speed and 5 minutes at high speed.

The resulting material was screened through a 60-mesh screen (U.S. Screen) to remove agglomerates, giving a yield of at least 90 percent. The final material was a dry free-flowing mass of coated microspheres, having a tacky, continuous or film-like coating of bonding material by which a layer of particles of bonding material was adhered to the microspheres.

A portion of the mass of coated microspheres was then placed in a mold and compacted at room temperature under a pressure of 200 pounds/square inch (14 kg/square cm) to prepare a cylinder 6 inches (15 cm) long with an outer diameter of 1 inch (2.5 cm). The resulting "green" compact was taken from the mold and heated to 400° F. (205° C.) for 10 minutes, whereupon the particles of bonding material melted, flowed, and cured.

The resulting cylinder (Sample A in Table I below) was about 25 percent porous and had a range of porosity as shown in FIG. 4. A similar cylinder was also prepared using microspheres that ranged from about 420 to 595 micrometers in diameter (Sample B).

The cylinders were then placed into containers such as represented by FIG. 1, with a two-inch length (5 cm) of the cylinder exposed outside the container. The container was filled with Reynaud's Jasmine fragrance. The weight of the container was measured initially and then at various intervals up to 159 days. The amount of weight loss in grams at various intervals is given in Table I. Since the fragrance was not diluted, nearly all of the lost weight represents fragrance dispensed into the air.

The amounts in Table I can be compared with results in Tables II–V which show the weight loss for a representative commercial fibrous wick dispenser (comprising a bottle of highly diluted fragrant liquid with the wick extending into the bottle and exposed two inches) (Table II); a representative commercial solid deodorant (a block of fragrance-impregnated organic crystals, which sublime into the air) (Table III); and a representative commercial gel-type room-freshener (believed to comprise 2–3 weight-percent of a mixture of essential oils such as oil of pine, wintergreen, etc., 1–2 weight-percent of gums such as carrageenan, a few percent of alcohol and emulsifier and approximately 90 weight-percent water) (Tables IV and V; Table IV shows the amount of total weight loss, while Table V shows the amount of fragrance lost, as measured by vapor phase chromatography; the Table IV and V tests were conducted in a closed system with an air flow of 650 cubic centimeters per minute).

The results obtained with Samples A and B of the present invention, and particularly Sample A, exhibit a superior uniformity in release of volatiles. When these results are compared with the results exhibited in Tables II–IV, the latter reveal a pronounced decline in weight loss over their period of use, and an uncontrolled and undesirable release of volatiles. The kind of result represented by Sample A and B is much preferred. Generally the weight loss from a dispenser of the invention after 75 days of use will be at least about 40 percent of the weight loss at the start of the test, and preferably at least about 75 percent of the weight loss at the start of the test.

TABLE I

INCREMENTAL WEIGHT LOSS AT DAY INDICATED
(grams)

| Day | Sample A | Sample B | Day | Sample A | Sample B |
|---|---|---|---|---|---|
| 2 | 0.50 | 0.56 | 41* | 0.45 | 0.39 |
| 3 | 0.66 | 0.54 | 43 | 0.48 | 0.32 |
| 6* | 0.42 | 0.41 | 45 | 0.37 | 0.33 |
| 8 | 0.41 | 0.38 | 48* | 0.39 | 0.27 |
| 9 | 0.37 | 0.36 | 49 | 0.40 | 0.30 |
| 13* | 0.33 | 0.30 | 51 | 0.42 | 0.30 |
| 15 | 0.45 | 0.38 | 52 | 0.45 | 0.31 |
| 20* | 0.36 | 0.35 | 55** | 0.44 | 0.30 |
| 22 | 0.43 | 0.39 | 56 | 0.40 | 0.28 |
| 24 | 0.39 | 0.37 | 58 | 0.42 | 0.30 |
| 28 | 0.38 | 0.36 | 59 | 0.39 | 0.28 |
| 30 | 0.40 | 0.41 | 62* | 0.40 | 0.27 |
| 34* | 0.48 | 0.43 | 77 | 0.42 | 0.24 |
| 36 | 0.56 | 0.47 | 159 | 0.39 | |

*First weighing after a weekend; air movement in the building where test was conducted is estimated to be 50 percent less during weekend

| DAY | TABLE II | TABLE III | TABLE IV | TABLE V |
|---|---|---|---|---|
| 1 | 14.35 | 6.44 | 7.41 | 0.150 |
| 2 | 19.34 | 8.06 | — | 0.168 |
| 3 | 18.60 | — | — | 0.054 |
| 4 | — | 8.51 | 3.70 | 0.048 |
| 5 | — | — | 3.94 | — |
| 7 | 14.40 | 10.39 | 3.51 | — |
| 8 | 12.07 | 12.12 | 3.40 | 0.057 |
| 9 | — | 10.28 | — | — |
| 10 | 3.79* | — | — | 0.045 |
| 11 | — | — | 2.59 | 0.024 |
| 12 | — | — | 2.53 | — |
| 13 | 4.72** | — | 2.62 | — |
| 14 | — | 9.74 | 1.96 | — |
| 15 | 1.89 | 12.61 | 2.22 | — |
| 16 | — | 11.13 | — | — |
| 17 | 0.85 | 9.72 | — | — |
| 18 | — | 9.75 | 2.31 | — |
| 19 | — | — | 2.40 | — |
| 20 | 0.59 | — | 3.47 | — |
| 22 | 0.43 | 8.93*** | 2.33 | — |
| 23 | — | 8.78 | — | — |
| 24 | — | 10.51 | — | — |
| 25 | — | — | — | — |
| 26 | — | — | — | — |
| 27 | 0.49 | 9.19 | 2.83 | — |
| 29 | — | 10.50 | — | — |
| 32 | — | — | 2.11 | — |
| 33 | — | — | 2.61 | — |
| 34 | — | — | 2.58 | — |
| 35 | — | — | 2.70 | — |
| 36 | — | — | 3.07 | — |
| 40 | — | — | 2.12 | — |

*Liquid level below wick. Lowered wick to reach liquid.
**All liquid gone from bottle. Loss just from liquid in wick.
***Significantly lowered fragrance level in room. For ordinary use judged to be ineffective.

What is claimed is:

1. A method for dispensing liquid comprising wicking said liquid into a wicking structure that comprises a matrix of closely packed, solid, rounded particles adhered together so as to leave an interconnected network of pores that occupies at least 20 volume-percent of the porous structure; the average diameter of said particles in the wicking structure being between 150 and 600 micrometers, and all said particles in the wicking structure having a diameter within plus-or-minus 20 percent of the average diameter of the particles, whereby the pores in the porous structure are uniform in size and the liquid is released from the porous structure at a uniform rate over an extended period of use; and exposing said wicking structure in the environment where it is desired to give off said liquid.

2. A method of claim 1 in which said porous structure is positioned in a container that contains an additional quantity of said liquid inside the container; the container being closed except for an opening adapted to tightly receive said wicking structure, with the wicking structure being positionable in the opening so that a portion is exposed outside the container and another portion extends into the liquid stored inside the container.

3. A method of claim 2 in which at least 50 weight-percent of said liquid consists of active volatile olfactory ingredients.

4. A vapor dispenser comprising a wicking structure and a volatile liquid stored in, and capable of wicking through, said wicking structure for release as vapor from the periphery of the structure; characterized in that the wicking structure comprises a matrix of closely packed, rounded solid particles adhered together so as to leave an interconnected network of pores that occupies at least 20 volume-percent of the porous structure; the average diameter of said particles in the wicking structure being between about 150 and 600 micrometers and all of said particles in the wicking structure having a diameter within plus-or-minus 20 percent of said average diameter, whereby the pores in the porous structure are uniform in size and the liquid is released from the porous structure at a uniform rate over an extended period of use.

5. A dispenser of claim 1 in which the dispenser further includes a container and an additional quantity of said volatile liquid inside the container; the container being closed except for an opening adapted to tightly receive said wicking structure, with the wicking structure being positionable in the opening so that a portion of the wicking structure is exposed outside the container and another portion extends into the volatile liquid stored inside the container.

6. A dispenser of claim 4 in which said particles are microspheres.

7. A dispenser of claim 4 in which at least 50 weight-percent of said volatile liquid consists of active olfactory ingredients.

8. A dispenser of claim 4 in which said particles are bonded together with a bonding material that comprises a cured organic material and that only partially fills the interstices between the particles so as to form said network of pores.

9. A dispenser of claim 4 in which said particles are individually coated over their exterior surface with a thin layer of bonding material, and those thin layers are fused together at their points of contact to adhere the particles together.

10. A dispenser of claim 4 in which said particles are between about 150 and 300 micrometers in diameter.

11. A dispenser comprising a wicking structure and a container that is closed except for an opening adapted to tightly receive said wicking structure, with the wicking structure being positionable in the opening so that a portion is exposed outside the container, and another portion extends into a liquid that is stored within the container, whereby the liquid can wick through the wicking structure for release from the periphery of the wicking structure; characterized in that the wicking structure comprises a matrix of closely packed, solid, discrete rounded particles bonded together with a bonding material that only partially fills interstices between the particles so as to form an interconnected network of pores that occupies at least 20 volume-percent of the porous structure; the average diameter of said particles in the wicking structure being between about 150 and 600 micrometers, and all of said particles in the wicking structure having a diameter within plus-or-minus 20 percent of said average diameter, whereby the pores in the porous structure are uniform in size and the liquid is released from the porous structure at a uniform rate over an extended period of use.

12. A dispenser of claim 11 in which said matrix particles are individually coated over their exterior surface with a thin layer of bonding material, and those thin layers are fused together at the point of contact of the coated particles to form a self-sustaining structure.

13. A dispenser of claim 11 in which said matrix particles are glass microspheres.

14. A dispenser of claim 11 in which said particles are between about 150 and 300 micrometers in diameter.

* * * * *